United States Patent

Descent

[11] Patent Number: 5,925,263
[45] Date of Patent: Jul. 20, 1999

[54] HANDHELD NEEDLE INCINERATOR FOR A DIABETES PEN-TYPE INJECTOR

[75] Inventor: Jacques Descent, Petersburg, Fla.

[73] Assignee: Biotronix 2000, Inc., Quebec, Canada

[21] Appl. No.: 08/936,109

[22] Filed: Sep. 23, 1997

[51] Int. Cl.[6] ............ B23K 11/22; A61G 12/00; A61L 11/00
[52] U.S. Cl. ............................................. 219/68
[58] Field of Search ................................. 219/68

[56] References Cited

U.S. PATENT DOCUMENTS

| | | | |
|---|---|---|---|
| 4,877,934 | 10/1989 | Spinello | 219/68 |
| 4,965,426 | 10/1990 | Colombo | 219/68 |
| 5,076,178 | 12/1991 | Kohl et al. | 219/68 |
| 5,091,621 | 2/1992 | Butler | 219/68 |
| 5,288,964 | 2/1994 | Walker et al. | 219/68 |
| 5,334,812 | 8/1994 | Hsieh | 219/68 |
| 5,710,404 | 1/1998 | Descent | 219/68 |
| 5,736,706 | 4/1998 | Butler | 219/68 |

FOREIGN PATENT DOCUMENTS

| | | |
|---|---|---|
| 2211420 | 7/1989 | United Kingdom . |
| 2300339 | 10/1996 | United Kingdom . |

Primary Examiner—Geoffrey S. Evans
Attorney, Agent, or Firm—Larson & Larson, P.A.; James E. Larson

[57] ABSTRACT

A handheld needle incinerator is self-contained within a portable housing and includes a guideway designed to guide the external walls of a diabetes pen-type injector into the incinerating chamber. Two spaced electrodes are simultaneously engaged by the needle to complete an electrical circuit and cause needle incineration. One electrode is dome-shaped and protrudes through an opening in the other electrode. Surrounding the opening in the other electrode is an annular generally conical surface designed to act like a ramp and lead the end of the needle toward the dome-shaped electrode to cause completion of the electrical circuit.

13 Claims, 4 Drawing Sheets

HANDHELD NEEDLE INCINERATOR FOR A DIABETES PEN-TYPE INJECTOR

BACKGROUND OF THE INVENTION

The present invention relates to a handheld needle incinerator for a diabetes pen-type injector. In the prior art, needle incinerators are known including those that are of a portable nature. Applicant is aware of the following prior art:

U.S. Pat. No. 4,877,934 to Spinello
U.S. Pat. No. 4,965,426 to Colombo
U.S. Pat. No. 5,076,178 to Kohl et al.
U.S. Pat. No. 5,091,621 to Butler
U.S. Pat. No. 5,334,812 to Hsieh.

The present invention differs from the teachings of these patents as contemplating a guideway for the exterior walls of a diabetes pen-type injector and also as contemplating electrodes consisting of a dome-shaped electrode protruding through a generally circular opening in another electrode, with the another electrode including generally conical walls surrounding the opening thereof.

In the prior art, the needle incinerators known to Applicant do not incinerate the entire needle. That is, when the incineration process has been completed, at least a small nub of the needle remains extending outwardly from the hub of the support thereof. This sharp nub presents the danger of spread of disease as well as the potential for injury to the user or others. In the present invention, to overcome this deficiency in the prior art, the needle is completely incinerated down to the hub structure.

SUMMARY OF THE INVENTION

The present invention relates to a handheld needle incinerator for a diabetes pen-type injector. The present invention includes the following interrelated objects, aspects and features:

(1) In a first aspect, the present invention is designed for use in incinerating a needle as retained on the hub end of a diabetes pen-type injector. One example of such a device comprises the Beckton Dickinson pen insulin delivery device, specifically designed for use with 1.5 ml cartridges of LILLY and NOVO NORDISK insulins. Such a device is generally in the shape of a writing pen and has a distal end with a coupling to which an injection needle assembly including a hub and needle may be removably installed.

(2) The inventive needle incinerator includes a small portable housing defining an incineration chamber that is connected outside the housing by a generally circular opening sized to guidingly receive the external walls of the pen-type injector.

(3) The circular opening leads to a guideway that narrows in the direction away from the circular opening to a circular terminus just proximal of the electrodes but within the incineration chamber of the inventive incinerator.

(4) The electrodes consist of a dome-shaped electrode including a proximal termination facing the circular terminus of the guideway and which protrudes through a circular opening formed through the other electrode.

(5) The other electrode includes conical walls surrounding its opening that are provided to guide a needle as attached to a pen-type injector toward the dome-shaped electrode. When the needle engages both of the electrodes simultaneously, a battery powered circuit is completed and the needle is incinerated.

(6) As the needle is being incinerated, the housing of the pen-type injector is successively pushed into the incineration chamber as guided by the circular opening and the circular terminus until the hub of the needle assembly engages the dome-shaped electrode thereby completing the incineration process.

Accordingly, it is a first object of the present invention to provide a handheld needle incinerator for a diabetes pen-type injector.

It is a further object of the present invention to provide such a device including a guideway to guide the outer walls of a pen-type injector toward the incineration electrodes of the device.

It is a still further object of the present invention to provide such a device including a dome-shaped electrode protruding through an opening in a flat electrode.

It is a yet further object of the present invention to provide the flat electrode with conical walls surrounding the opening thereof.

These and other objects, aspects and features of the present invention will be better understood from the following detailed description of the preferred embodiment when read in conjunction with the appended drawing figures.

SPECIFIC DESCRIPTION OF THE PREFERRED EMBODIMENT

Figure 1:
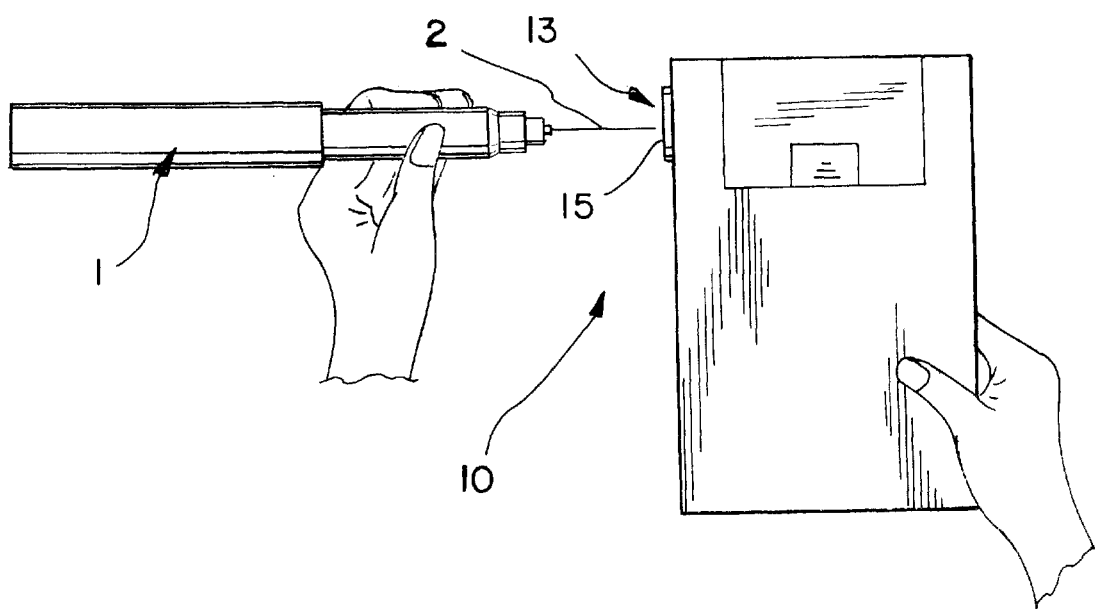
FIG. 1 shows a longitudinal cross-sectional view through pertinent portions of the inventive incinerator.

With reference, first, to FIG. 1, the present invention is generally designated by the reference numeral 10 and is seen to include a portable housing 11 having a generally circular opening 13 further defined by a ring 15 affixed on the outer surface thereof In the distal direction from the opening 13, the housing 11 has inner walls 17 and 19 defining, therebetween, an incineration chamber 21.

The inner wall 17 has a generally circular opening 23. An inner surface 18 of inner wall 17 has affixed to it a guideway 25 that includes a proximal generally cylindrical section 27 having a generally cylindrical inner wall 29 and a distal generally conical section 31 having an inner generally conical wall 33. The guideway 25 terminates in the distal direction with an exit or terminus opening 35 within the incineration chamber 21.

As seen in FIG. 1, within the incineration chamber 21, two electrodes are installed, a first electrode 37 having a dome-shaped proximal surface 39 protruding within a generally circular opening 43 of a second electrode 41. The electrode 41 is L-shaped in configuration having a first leg 45 mounted on a wall 22 of the incineration chamber 21 with a screw 47. The second leg 49 (FIG. 3) is generally rectangular in configuration with the opening 43 being generally centrally located thereon.

Figure 2:
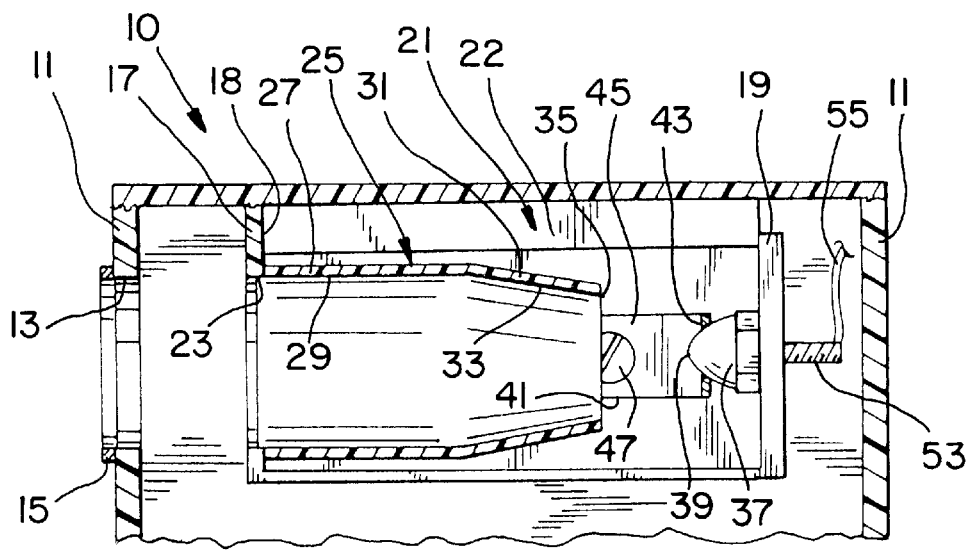
FIG. 2 shows an enlarged view of a portion of the view of FIG. 1 with the addition of schematic electrical circuitry details.
Figure 4:
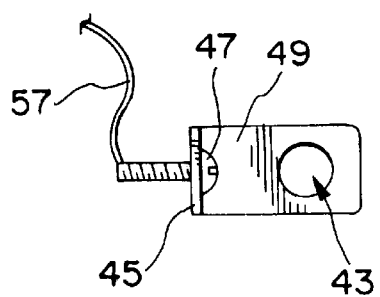
FIG. 4 shows a view similar to that of FIG. 3 but looking more proximally than FIG. 3.

With reference to FIG. 2, it is seen that the leg 49 includes annular conical surfaces 51 surrounding the opening 43 and which define a ramp-like surface converging in the distal direction and designed to lead a needle down the surface and to the opening 43 and thence through the opening 43 and into engagement with the dome-shaped surface 39 of the electrode 37. FIG. 4 shows the ring 15, the terminus opening 35, the rectangular leg 49, and the opening 43 and explains the juxtaposition of these elements of the present invention.

Figure 3:
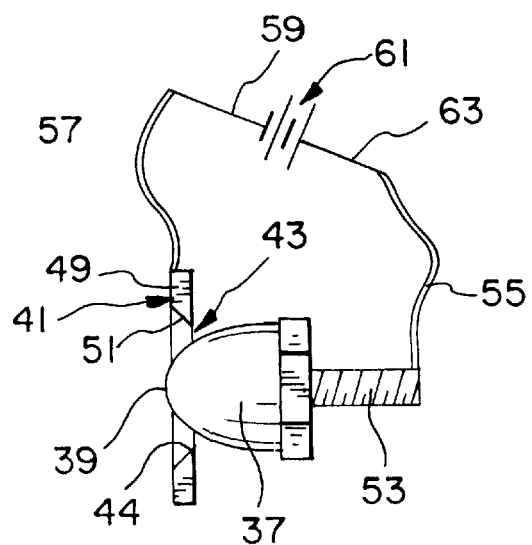
FIG. 3 shows an enlarged end view of a portion of the structure of FIG. 1.

With reference to FIGS. 1–3, it is seen that the electrode 37 includes a mounting post 53 that is connected to structure (not shown) to fix the electrode 37 in mounted position. An electrical conductor 55 is soldered or otherwise electrically connected to the mounting post 53. If desired, the mounting post 53 may be threaded as shown. The electrode 41 includes an electrical conductor 57 attached to the end of the screw 47 by any suitable means. The conductor 57 is schematically shown in FIG. 2 to be generally connected to the electrode 41 and to make an electrical circuit with the wire 59, power supply 61, wire 63, and conductor 55. As should be understood from FIG. 2, the opening 43 is defined by the knife edge 44 of the surface 51 and the dome-shaped surface 39 of the electrode 37. An electrically conductive material interconnecting the electrodes within the opening 43 will complete this circuit. The power supply 61 may comprise one or more DC batteries.

Figure 5:
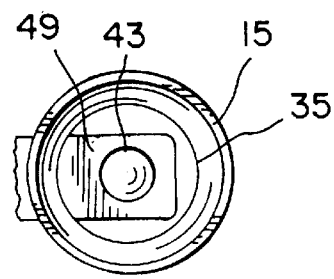
FIGS. 5, 6 and 7 show the sequence of operation of the present invention when a pen-type injector with a needle attached thereto is inserted into the incineration chamber thereof.
Figure 6:
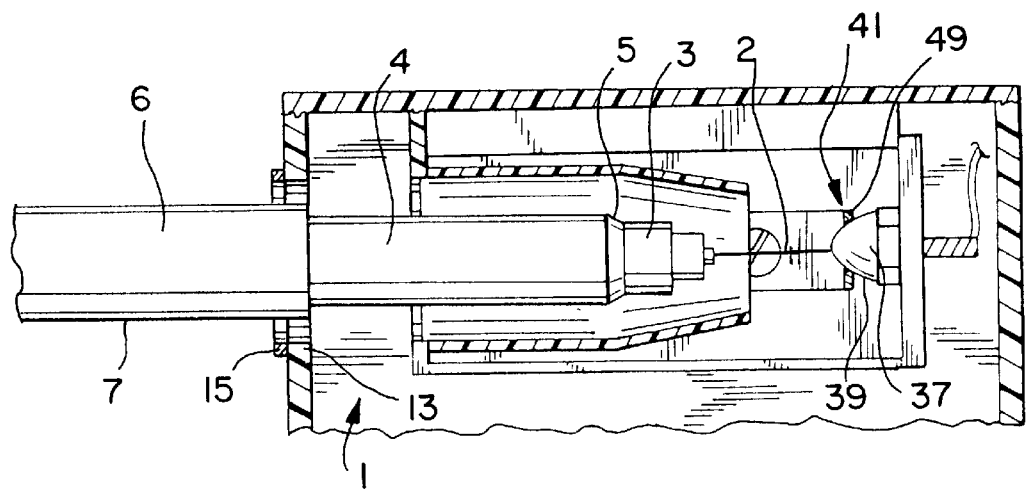
Figure 7:
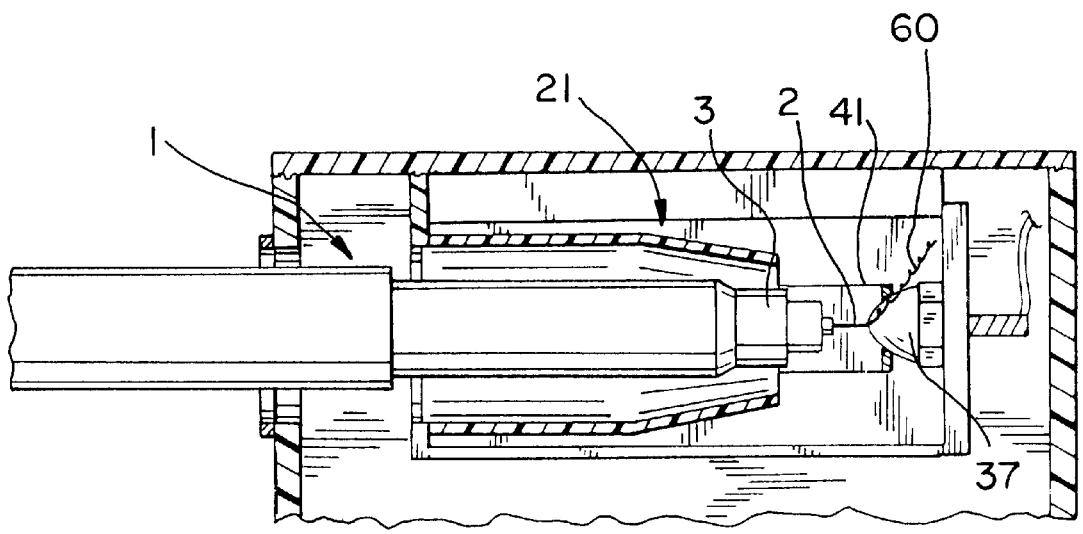

With reference to FIGS. 5, 6 and 7, the operation of the present invention will now be described. In particular, with reference to FIG. 5, a pen-type injector 1 is seen to have a needle 2 and a needle hub 3 mounted on the distal end 5 of a barrel 4 by suitable means such as, for example, complementary threads. The barrel 4 leads to a wider gripping portion 6 having outer surfaces 7.

In the position shown in FIG. 5, the surfaces 7 engage the ring 15 at the opening 13 and guide inwardly directed movements of the device 1 into the incineration chamber 21. In the position shown in FIG. 5, the distal end of the needle 2 is touching the surface 39 of the electrode 37 but is spaced from the leg 49 of the electrode 41. With reference to FIG. 6, it is seen that further inward movement of the device 1 results in flexing of the needle 2 and engagement with both the electrode 37 and the electrode 41 causing incineration of the needle 2 with the reference numeral 60 referring to smoke emanating from the needle 2 as it is incinerated.

Figure 8:
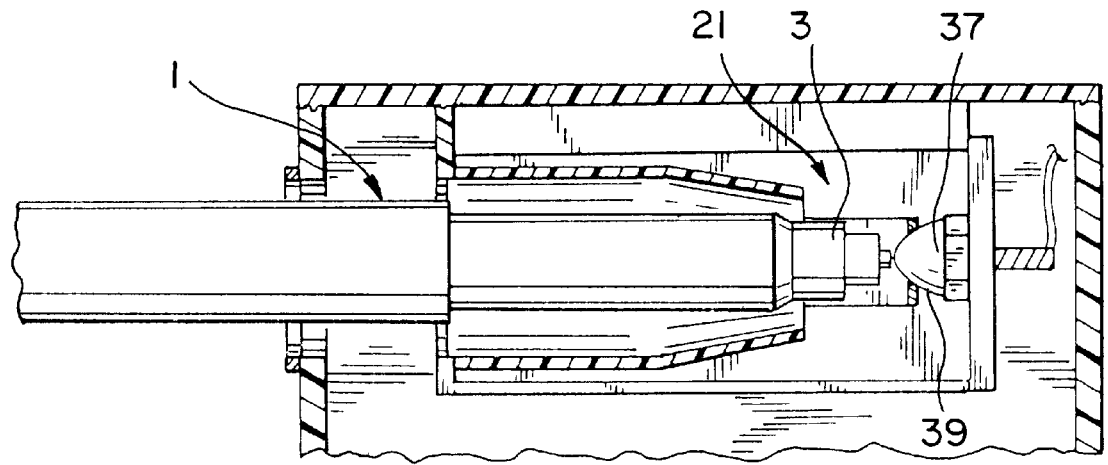
FIG. 8 shows the pen-type injector with the needle burned away.

With reference to FIG. 7, as the device 1 is pushed further into the incineration chamber 21, the needle 2 continues to incinerate until the distal end of the hub 3 engages the most proximal portion of the dome-shaped surface 39 of the electrode 37. When this occurs, the incineration process is complete and the proximal surface of the electrode 37 acts as a limit stop preventing further intrusion of the device 1 into the incineration chamber 21 as shown in FIG. 8.

The device 1 may thereafter be backed out of the chamber 21 and removed therefrom completely with the hub 3 being removed from the barrel 4 and being suitably discarded.

Once the needle has been completely incinerated, the circuit described above is thereby opened since there is no needle left to make a connection within the opening 43 between the electrodes 37 and 41.

If desired, the guideway 25, housing 11, and ring 15 may be made of any suitable plastic material.

Accordingly, an invention has been disclosed in terms of a preferred embodiment thereof which fulfills each and every one of the objects of the present invention as set forth hereinabove and provides a new and useful handheld needle incinerator for a diabetes pen-type injector of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

I claim:

1. A handheld needle incinerator, comprising:
 a) a handheld housing having an opening allowing access to an incineration chamber;
 b) incineration electrodes within said chamber including:
  (i) a first electrode having a generally dome-shaped surface facing said opening;
  ii) a second electrode having an electrode opening aligned with said dome-shaped surface;
  iii) said dome-shaped surface protruding into said electrode opening.

2. The needle incinerator of claim 1, further including a guideway extending from just within said housing opening to a location within said incineration chamber.

3. The needle incinerator of claim 2, wherein said guideway has a distal circular terminus opening adjacent said electrodes.

4. The needle incinerator of claim 3, wherein said guideway has a proximal cylindrical wall connected to a conical wall terminating at said terminus opening, said housing opening and guideway being configured to guide movements of an injector within said housing.

5. The needle incinerator of claim 1, wherein said second electrode is L-shaped having a first leg affixed to a wall of said incineration chamber and a second leg orthogonal to said first leg, said second leg having said electrode opening therethrough.

6. The needle incinerator of claim 5, wherein said electrode opening includes annular conical surfaces converging in a direction toward said first electrode.

7. The needle incinerator of claim 1, wherein said electrode opening includes annular conical surfaces converging in a direction toward said first electrode.

8. The needle incinerator of claim 1, wherein a small gap is defined between said electrode opening and said dome-shaped surface.

9. The needle incinerator of claim 1, wherein said dome-shaped surface has a proximal terminus comprising a limit stop limiting distal movement of a hub of a needle assembly of a pen-type injector.

10. A handheld needle incinerator, comprising:
 a) a handheld housing having a circular opening allowing access to an incineration chamber;
 b) incineration electrodes within said chamber including:
  i) a first electrode having a generally dome-shaped surface facing said opening;
  ii) a second L-shaped electrode having a first leg with a circular electrode opening therethrough aligned with said dome-shaped surface, and a second leg orthogonal to said first leg and affixed to a wall of said incineration chamber;
  iii) said dome-shaped surface protruding into said electrode opening;
 c) a guideway extending from just within said housing circular opening to a location within said incineration chamber, said guideway having a distal circular terminus opening adjacent said electrodes, and a proximal cylindrical wall connected to a conical wall terminating at said terminus opening, said housing opening and guideway being configured to guide movements of an injector within said housing.

11. The needle incinerator of claim 10, wherein said electrode opening includes annular conical surfaces converging in a direction toward said first electrode.

12. The needle incinerator of claim 10, wherein a small gap is defined between said electrode opening and said dome-shaped surface.

13. The needle incinerator of claim 10, wherein said dome-shaped surface has a proximal terminus comprising a limit stop limiting distal movement of a hub of a needle assembly of an injector.

* * * * *